United States Patent
Carron

(10) Patent No.: US 10,206,563 B2
(45) Date of Patent: Feb. 19, 2019

(54) DENTAL MIRROR

(71) Applicant: AVID, Inc., Bloomsdale, MO (US)

(72) Inventor: Chris J. Carron, Bloomsdale, MO (US)

(73) Assignee: AVID, Inc., Bloomsdale, MO (US)

( * ) Notice: Subject to any disclaimer, the term of this patent is extended or adjusted under 35 U.S.C. 154(b) by 208 days.

(21) Appl. No.: 15/099,019

(22) Filed: Apr. 14, 2016

(65) Prior Publication Data

US 2016/0302655 A1 Oct. 20, 2016

Related U.S. Application Data

(60) Provisional application No. 62/149,035, filed on Apr. 17, 2015.

(51) Int. Cl.
*A61B 1/253* (2006.01)
*A61B 1/00* (2006.01)
*A61B 1/06* (2006.01)
*A61B 1/12* (2006.01)

(52) U.S. Cl.
CPC .......... *A61B 1/253* (2013.01); *A61B 1/00016* (2013.01); *A61B 1/00066* (2013.01); *A61B 1/00103* (2013.01); *A61B 1/00105* (2013.01); *A61B 1/00128* (2013.01); *A61B 1/06* (2013.01); *A61B 1/126* (2013.01); *A61B 1/00032* (2013.01)

(58) Field of Classification Search
CPC ... A61B 1/2553; A61B 1/247; A61B 1/00016; A61B 1/00066; A61B 1/00103; A61B 1/00105; A61B 1/00128; A61B 1/06; A61B 1/123; A61B 1/00032
See application file for complete search history.

(56) References Cited

U.S. PATENT DOCUMENTS

| | | | | |
|---|---|---|---|---|
| 2,686,456 A | * | 8/1954 | Szuba | A61B 1/247 359/882 |
| 3,539,247 A | * | 11/1970 | Broussard | A61B 1/253 359/507 |
| 4,266,933 A | * | 5/1981 | Warden | A61C 17/005 222/161 |
| 4,420,762 A | * | 12/1983 | Andrews | G01D 15/24 346/136 |
| 5,902,105 A | * | 5/1999 | Uejima | A61C 19/041 433/27 |
| 7,766,656 B1 | * | 8/2010 | Feine | A61C 5/62 433/89 |
| 2004/0076019 A1 | * | 4/2004 | Tsimerman | A61B 1/00096 362/580 |
| 2005/0244788 A1 | * | 11/2005 | Feine | A61C 3/03 433/165 |

* cited by examiner

*Primary Examiner* — Heidi M Eide
(74) *Attorney, Agent, or Firm* — Harness, Dickey & Pierce, P.L.C.

(57) ABSTRACT

A dental mirror includes a handle having a lumen, a mirror housing attached to the handle, a mirror cartridge for insertion through a cartridge opening of the mirror housing, a drive shaft rotatably held within the handle, and a film-roller rotatably attached to a film-roller bearing. The mirror cartridge includes a base, a film-roller bearing connected to the base, a film support structure connected to the base, and a film surrounding the film support structure. A distal end of the drive shaft and a proximal end of the film-roller are rotatably linked such that a rotation of the drive shaft rotates the film-roller causing the film to move relative to the film support structure.

34 Claims, 7 Drawing Sheets

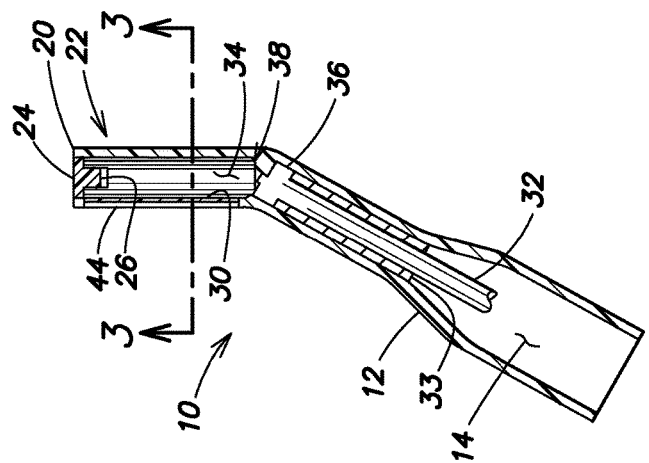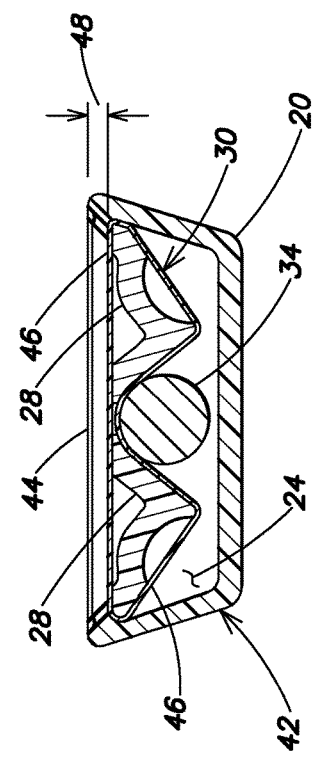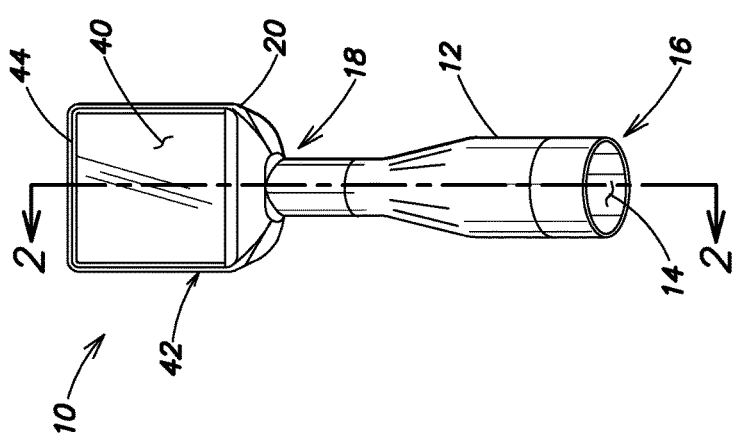

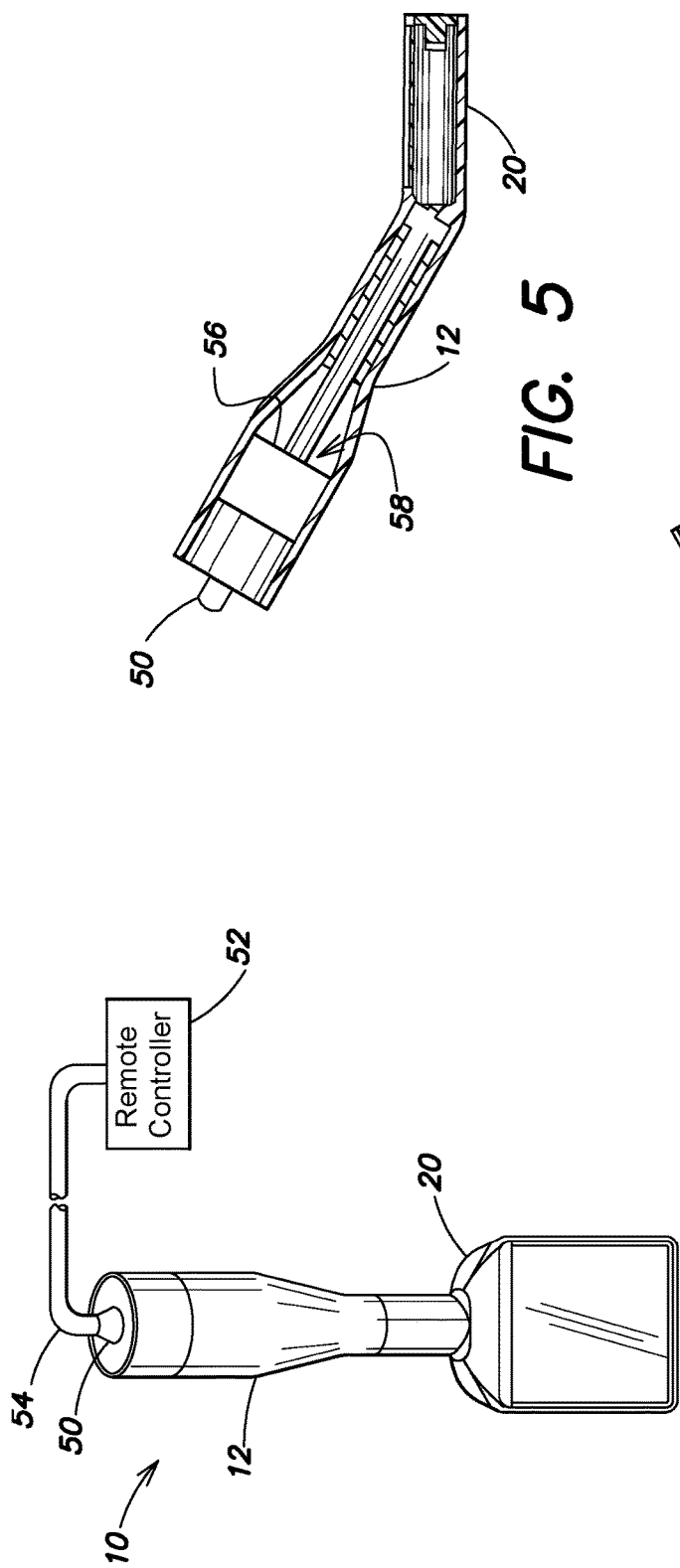

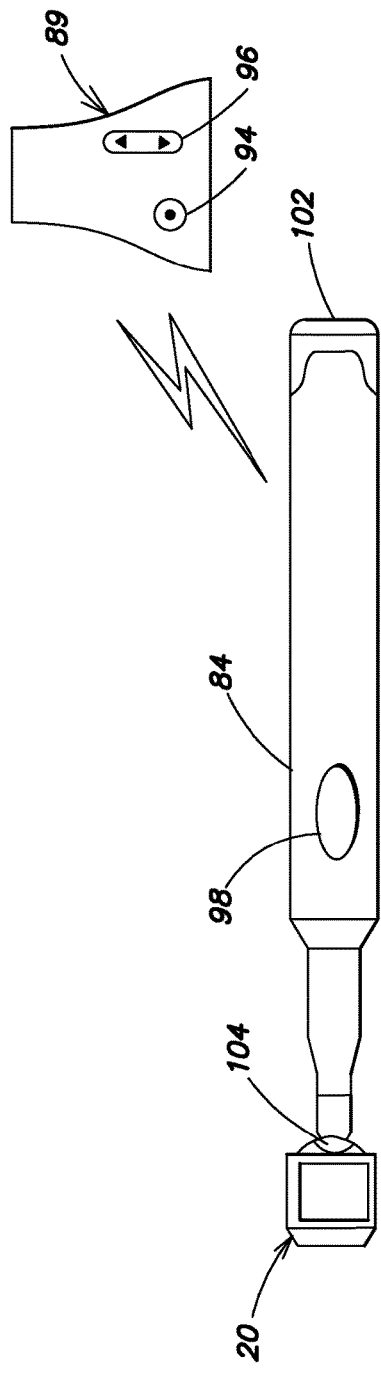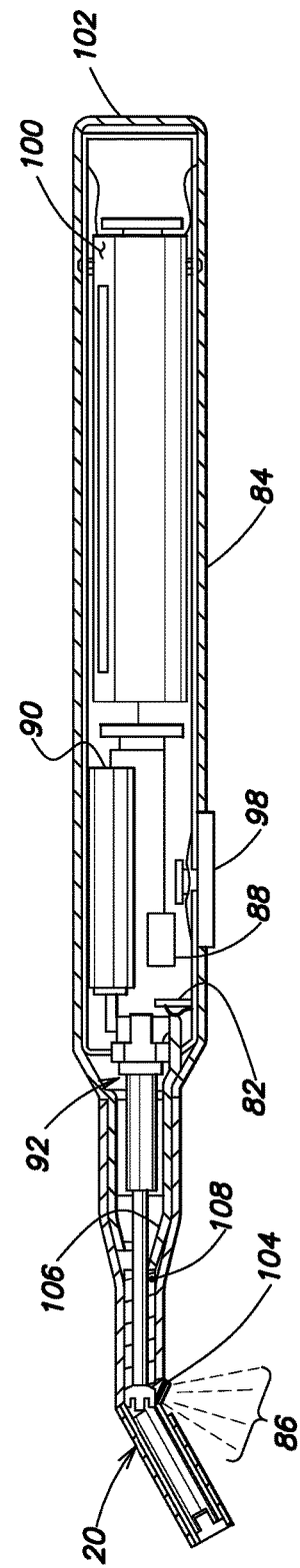

DENTAL MIRROR

CROSS-REFERENCE TO RELATED APPLICATIONS

Figure 7:
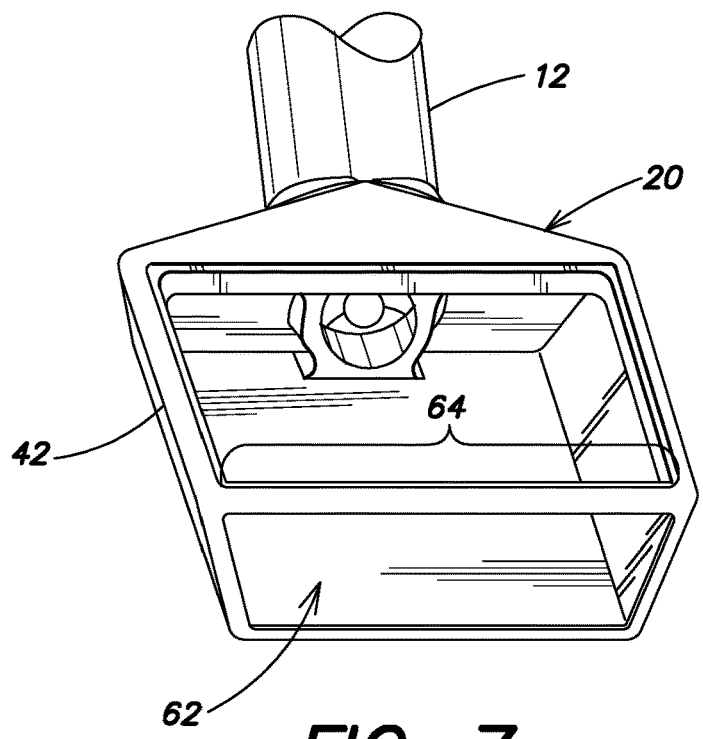

This patent application claims the benefit of and priority to U.S. Provisional Patent Application No. 62/149,035 filed Apr. 17, 2015. The entire disclosure of the above application is incorporated herein by reference.

FIELD

The present disclosure relates to dental instruments. More specifically, the present disclosure relates to dental mirrors, particularly dental mirrors including a movable film.

BACKGROUND

This section provides background information related to the present disclosure which is not necessarily prior art.

Hand-held mirrors are commonly used by dentists. During use, the mirrors easily become ineffective because of fogging or from being obscured by debris or moisture. This may interrupt the dental procedure, requiring periodic cleaning of the mirror or the use of multiple mirrors for a single procedure.

A manually operated mirror is known that includes a film that can be moved periodically to present a clean, unobscured reflective surface for effective viewing by the dentist. The film may be transparent, overlaying a mirror surface or the film itself may be reflective.

But the known prior art dental mirrors are formed of many piece parts resulting in expensive assembly costs during manufacture. Further, the replacement of the film may be difficult; either requiring a partial disassembly of the mirror or installing a new film onto reels mounted within a tight confined space. Therefore, the inventor hereof has recognized that a need exists for an effective, economical dental mirror.

SUMMARY

This section provides a general summary of the disclosure, and is not a comprehensive disclosure of its full scope or all of its features.

One example embodiment discloses a dental mirror with a handle with a mirror housing attached to the handle. A mirror cartridge is inserted through a cartridge opening of the mirror housing. The mirror cartridge may include a base, a film-roller bearing connected to the base, a film support structure connected to the base, and a film surrounding the film support structure. A drive shaft is rotatably held within the handle. A film-roller is rotatably attached to the film-roller bearing. A distal end of the drive shaft and a proximal end of the film-roller are rotatably linked such that a rotation of the drive shaft rotates the film-roller causing the film to move relative to the film support structure.

An example mirror cartridge embodiment for insertion into a dental mirror may include a base, a film-roller bearing connected to the base, a film support structure connected to the base, a film surrounding the film support structure.

Another example embodiment of a dental mirror may include a handle and a mirror housing attached to the handle. A mirror cartridge may be held within a cartridge opening of the mirror housing. The mirror cartridge may include a base, a film-roller rotatably attached to the base, a film support structure connected to the base, at least one elongated bearing member connected to the base, and a film surrounding the film support structure. A drive shaft may be rotatably held within the handle.

A distal end of the drive shaft and a proximal end of the film-roller may be rotatably linked such that a rotation of the drive shaft rotates the film-roller causing the film to move relative to the film support structure. Further a hydrophilic material may be attached to at least a portion of the at least one elongated bearing member such that the hydrophilic material contacts a film top surface.

Example embodiments may also include an illumination source and may include a motor for driving the film roller. The motor and/or the illumination source may be activated by a user via one or more switches on the handle or via a remote control fob by an assistant. Further, the motor, illumination source, battery, and other electrical components may be held within a removable cartridge.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Figure 8:
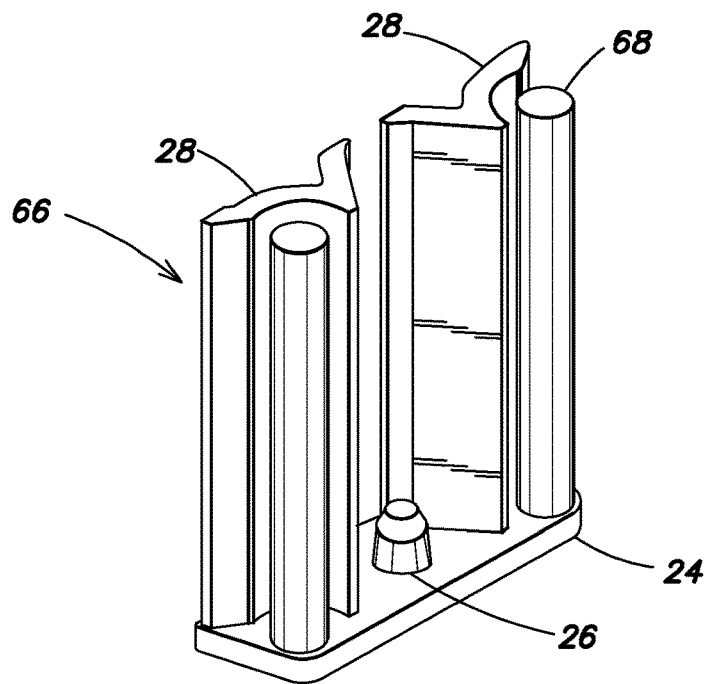
Figure 9:
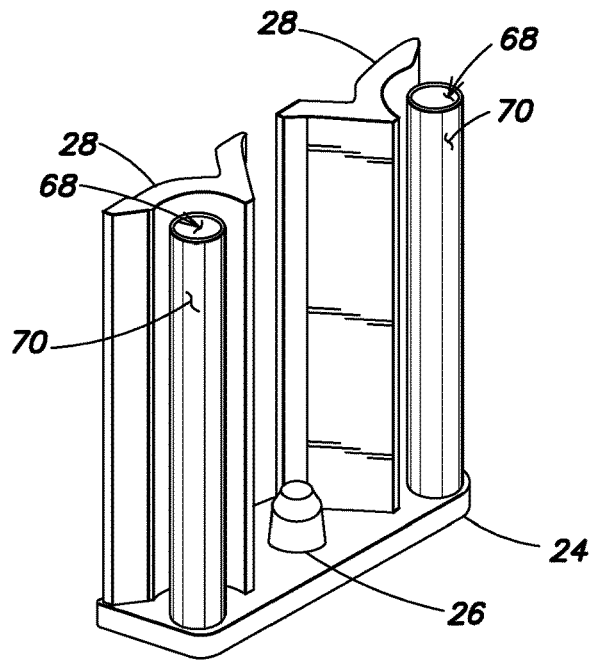
Figure 10:
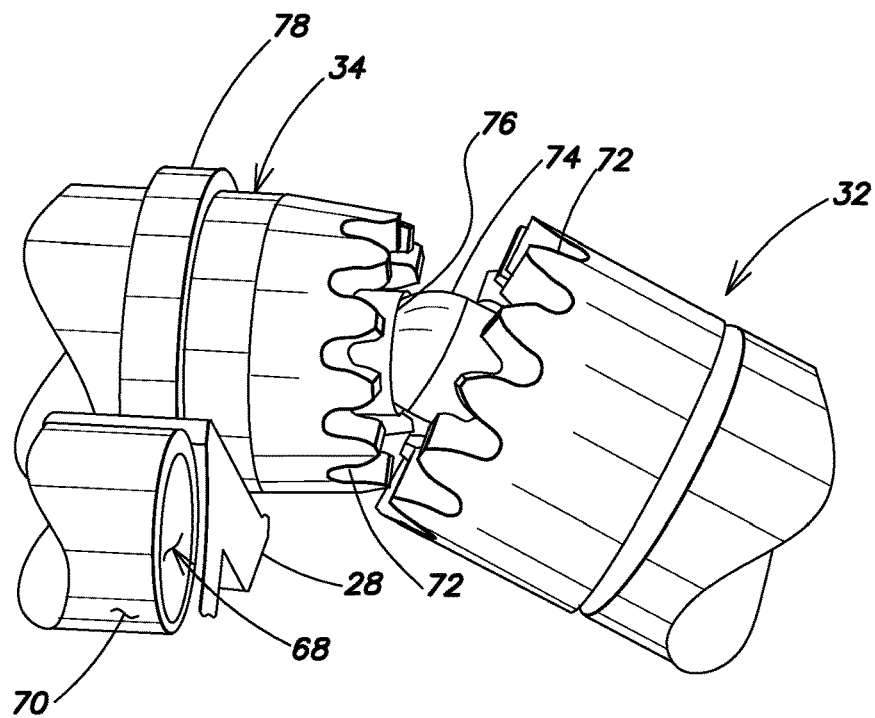
Figure 11:
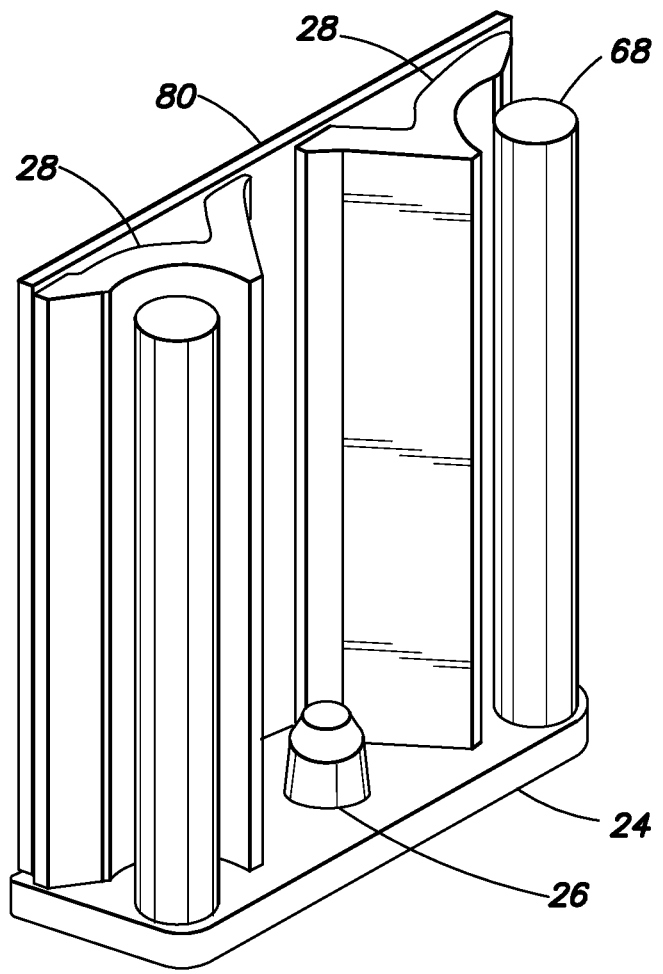
Figure 12:
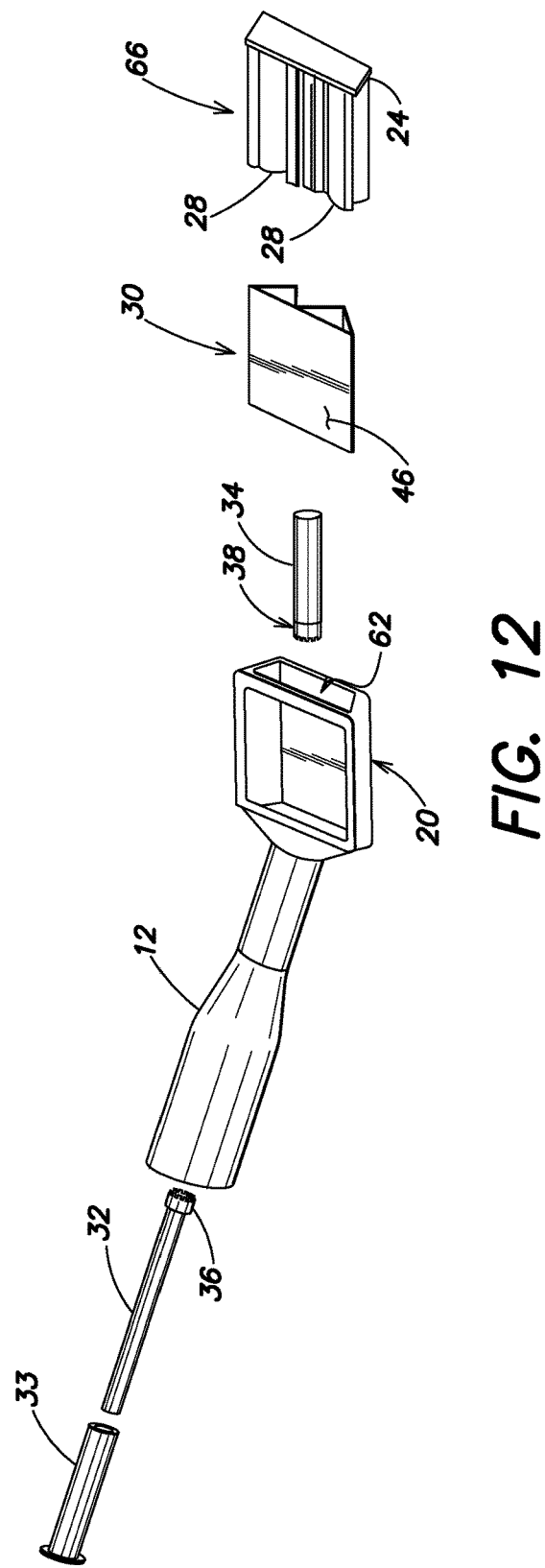

FIG. 1 is a perspective view of an example embodiment;
FIG. 2 is a cross-section of FIG. 1 taken along line 2-2;
FIG. 3 is a cross-section of FIG. 2 taken along line 3-3;
FIG. 4 is a modified block diagram of an example system for use with an example dental mirror;
FIG. 5 is a cross-section of another example embodiment;
FIG. 6 is a side elevation of yet another example embodiment;
FIG. 7 is a partial perspective of an example embodiment;
FIG. 8 is a perspective of a portion of an example mirror cartridge;
FIG. 9 is a perspective of a portion of another example mirror cartridge;
FIG. 10 is a partial perspective view of an example rotatable link of an example embodiment;
FIG. 11 is a perspective of a portion of yet another example mirror cartridge;
FIG. 12 is an exploded perspective of an example embodiment;
FIG. 13 is a top view a further example embodiment; and
FIG. 14 is a cross-section of a portion of FIG. 13.

Corresponding reference numerals indicate corresponding parts throughout the several views of the drawings.

DETAILED DESCRIPTION

Example embodiments will now be described more fully with reference to the accompanying drawings.

A dental mirror 10 is shown in FIG. 1. The dental mirror 10 may include a handle 12 having a lumen 14 extending from a handle proximal end 16 to a handle distal end 18. A mirror housing 20 may be attached to the handle distal end 18, as shown.

FIG. 2 shows a cross-section of the dental mirror taken along line 2-2 of FIG. 1. A mirror cartridge 22 for insertion through a cartridge opening (not shown) of the mirror housing 20 may include a base 24, a film-roller bearing 26 connected to the base 24, a film support structure 28 (best seen in FIG. 3 and other figures) connected to the base 24, and a film 30 surrounding the film support structure 28, as shown in FIGS. 2 and 3. The term "surrounding", as used in this disclosure, should be understood to include the belt-type film 30 disclosed, as well as a reel-to-reel type of film that is unwound from a first reel and wound onto a second reel.

As shown in FIG. 2, dental mirror 10 may also include a drive shaft 32 rotatably held within the handle 14 and a film-roller 34 rotatably attached the film-roller bearing 26. A distal end 36 of the drive shaft 32 and a proximal end 38 of the film-roller 34 may be rotatably linked such that a rotation of the drive shaft 32 rotates the film-roller 34 causing the film 30 to move relative to the film support structure 28. In this way, a new clean section of film may be moved into the reflective viewing area of film opening 40 (clearly shown in FIG. 1), after a section of film has been obscured by moisture and/or debris. The mirror housing 20 may further include a peripheral frame 42 defining the film opening 40 for exposing a portion of the film 30 and a top surface 44 of the peripheral frame 42 may be formed above a film top surface 46, as indicated at 48. The raised top surface 44 of peripheral frame 42 provides a measure of protection against inadvertent contact with moist tissue of a patient's mouth and may help prolong the effective useful life of a section of film 30 during a procedure. The drive shaft 32 may further include a sleeve bearing 33 surrounding at least a portion of the drive shaft 32 to assist in reliably locating and retaining the drive shaft 32 within the handle 12.

The handle 12 may further include a connector 50, shown in FIG. 4, for connecting the handle 12 to a remote controller 52 for causing the drive shaft 32 to rotate via cable 54. For example, a remote controller may form a part of a dental instrument control system and a handle activation device, such as a foot controller (not shown), may cause the drive shaft 32 to rotate via a motor housed in either the handle 12 or the remote controller 52. In another example embodiment, shown in FIG. 5, the handle 12 may include a motor 56 connected to a drive shaft proximal end 58, and the connector 50 may be attached to the motor 56 for receiving power from the remote controller 52. In yet another example embodiment, the connector 50 may be attached to the drive shaft proximal end 58 and the connector 50 may be for connection to a cable 54 that may be a drive cable that is caused to be rotated by the remote controller 52. Other drive schemes such as pneumatic drives may also be used, e.g., any appropriate way to cause drive shaft 32 to rotate may be acceptable. A still further example embodiment, shown in FIG. 6, the handle 12 may include a knob 60 connected to the drive shaft proximal end 58 for manually rotating the drive shaft 32. The type of drive mechanism or scheme depends on the preference of the user and the design requirements. A power driven drive shaft provides the benefit of single handed use of dental mirror 10 by allowing the film to be rotated via the use of a foot pedal, voice control, or other interface. This allows the dentist to remain concentrated on the procedure without the distraction and delay of requiring a second hand to move the film.

FIG. 7 shows an example embodiment where the structure of the mirror housing 20 defining the cartridge opening 62 includes a portion of the peripheral frame 42 as indicated at 64. This frame portion at 64 provides strength and rigidity to mirror housing 20 and allows the mirror cartridge 22 to be securely held in mirror housing 20 without the need for additional fasteners. The mirror cartridge 22 may be removably attached to the mirror housing 20 without the use of tools; thus allowing the handle 12 and mirror housing 20 to be reused with a new, clean, sterile mirror cartridge. Alternatively, mirror cartridge 22 may be permanently mounted within cartridge opening 62 via any known manner such as friction fit, snap fits, or adhesive. Cartridge opening 62 is shown at the distal end of mirror housing 20 but may be formed in mirror housing 20 at other locations, such as either side or the side adjacent handle 12, or even in the bottom of mirror housing 20.

The base 24, the film-roller bearing 26, and the film support structure 28 may be molded (e.g., injection molded, etc.) as a unitary piece. The handle 12 and the mirror housing 20 may also be molded as a unitary piece. This eliminates the need for several fasteners, allows the film to be easily loaded and unloaded from the mirror housing 20, and allows for significant manufacturing cost reductions, compared to the known prior art.

As shown in FIG. 8, an alternate example mirror cartridge 66 is the same as cartridge 22 with the addition that mirror cartridge 66 may include at least one elongated bearing member 68 connected to the base 24 and in contact with the film top surface 46 (film is not shown for clarity). Mirror cartridge 66 may also include two elongated bearing members 68, as shown. The elongated bearing members 68 may also be molded with base 24, bearing 26, and film support structure 28 as a unitary piece. Elongated bearing members 68 may provide guidance and tensioning to the film 30 and may also assist in removing moisture and debris from the film top surface 46 during use.

Additionally, a hydrophilic material may be attached to at least a portion of the at least one elongated bearing member 68 for absorbing moisture from the film top surface 46. The hydrophilic material may be attached to the portion of elongated bearing member 68 that contacts the film top surface 46 and the attachment may be realized by any appropriate means, such as adhesives. FIG. 9 shows another example embodiment where the hydrophilic material forms a cylinder 70 that may be rotatably mounted on the at least one elongated bearing member 68 such that the cylinder 70 rotates as the film (not shown) moves. The hydrophilic material may be any material that readily attracts and absorbs moisture, e.g., cotton, felt, sponge, chamois, or other materials.

As shown in FIG. 10, the drive shaft 32 and the film-roller 34 may be rotatably linked by gears, such as the face gears at 72. Additionally, the drive shaft 32 and film-roller 34 may include a pivot structure for maintaining reliable positioning with respect to each part. For example, the pivot structure may be the mating hemispherical protrusion 74 and socket 76. Other drive and positioning schemes may be employed. For example, in place of the face gears 72, the hemispherical protrusion 74 could be formed as a hex key that mates with a hex socket. In this way, both the positioning and the drive mechanism may be formed by a single structure. FIG. 10 also clearly shows an annular boss 78 formed on the film-roller 34. The boss 78 may enhance frictional contact with the film 30 and enhance the reliability of moving the film 30 when the film-roller 34 rotates. Boss 78 may also have other form, e.g. boss 78 may be formed as a gear tooth pattern where each tooth is for engagement with a series of holes formed along the length of the film 30.

The film 30 may be formed from a flexible reflective material such as polyethylene terephthalate (PET), e.g. Mylar®, or other suitable reflective material such that film 30 forms the mirror. Alternatively, the film 30 may be transparent and a mirror surface 80 may be formed on a portion of the film support structure 28 as shown in FIG. 11. In addition, the film 30 may be treated with an appropriate hydrophobic coating to help maintain a sufficient reflective viewing surface. As is known, hydrophobic coatings promote beading of fluid, thus limiting the amount of fluid that will adhere to the film and interfere with viewing objects and tissue reflected by the mirror surface.

The disclosed dental mirror examples may be particularly applicable to single-use, disposable dental mirrors because the design allows for the manufacture of inexpensive molded piece parts that can be assembled quickly without the need for many tools, jigs, and little specialized training. Each part may be molded or formed of appropriate materials. For example, the drive shaft 32 and bearing sleeve 33 may be formed of material such as acetal resin, e.g. Delrin® or other material that provides sufficient rigidity yet allows the drive shaft 32 to easily rotate within the bearing sleeve 33. In order to ensure a single use and prevent any contamination from patient to patient, at least a portion of the mirror cartridge 22 may be formed of a material that will not withstand autoclave sterilization but yet provides the functionality required, e.g. certain types of Delrin®. In addition or as an alternative, at least one of the handle and the mirror housing may be formed of a material that will not withstand autoclave sterilization. Also, the shape of the film support structure 28 should allow for the film 30 to easily slide over and around the support structure 28 so that the film is easily moved by the film-roller 34. The film-roller 34 may be formed of a material that provides sufficient rigidity to engage with and be driven by drive shaft 32 and also exhibit good frictional contact with the film 30 so that the film 30 is easily moved by rotation of the film-roller 34.

Also, illumination may be added to the dental mirror 10. For example, an illumination source such as an LED may be housed within the handle 12 and coupled to a fiber or tube to direct light towards the mirror housing 20. Alternatively, the illumination source could reside within remote controller 52 with a light guide directing light from the illumination source to the dental mirror 10.

One example dental mirror may include a handle having a lumen extending from a distal end to a proximal end, a mirror housing attached to the handle proximal end, a mirror cartridge held within a cartridge opening of the mirror housing, and a drive shaft rotatably held within the handle. The mirror cartridge may include a base, a film-roller rotatably attached to the base, a film support structure connected to the base, at least one elongated bearing member connected to the base, and a film surrounding the film support structure. A distal end of the drive shaft and a proximal end of the film-roller may be rotatably linked such that a rotation of the drive shaft rotates the film-roller causing the film to move relative to the film support structure. The mirror cartridge may also include a hydrophilic material attached to at least a portion of the at least one elongated bearing member such that the hydrophilic material contacts a film top surface.

A method of assembling the dental mirror 10 is described with reference to FIG. 12 that shows an example dental mirror in exploded form. Assembly may begin with providing a mirror cartridge 66 that may include a base 24, a film-roller bearing (not shown) connected to the base 24, and a film support structure 28 connected to the base 24. The next step may be inserting a film 30 over the film support structure 28; followed by rotatably mounting a film-roller 34 onto the film-roller bearing. Next may be the step of inserting the mirror cartridge 66 into a cartridge opening 62 of a mirror housing 20. The base 24 may be configured so to correspond in shape and size (e.g., have a similar size and trapezoidal shape, etc.) as the cartridge opening 62 such that the base 24 closes and/or seals off the cartridge opening 62 after the mirror cartridge 66 has been inserted into the cartridge opening 62. Accordingly, the base 24 may also function as an end cap for the mirror housing 20, thereby eliminating the need to attach a separate end cap to the mirror housing 20.

Final assembly may include inserting a drive shaft 32 into a lumen of a handle 12 connected to the mirror housing 20 such that a distal end 36 of the drive shaft 32 and a proximal end 38 of the film-roller 34 are rotatably linked. Once assembled, a rotation of the drive shaft 32 rotates the film-roller 34 causing the film 30 to move relative to the film support structure 28.

In this example, the drive shaft 32 may be "bottom" loaded into the handle 12 by inserting the drive shaft 32 through a bottom or distal open end of the handle 12. Insertion of the drive shaft 32 may continue until the distal end 36 of the drive shaft 36 sufficiently passes through a thru-hole or opening between the handle 12 and mirror housing 20 and the distal 36 end of the drive shaft 32 engages the proximal end 38 of the film-roller 34. Also in this example, the mirror cartridge 66 may be "top" loaded into the mirror housing 20 by inserting the mirror cartridge 66 through the cartridge opening 62, which is shown at the top of the mirror housing 20 in FIG. 12. Accordingly, the drive shaft 32 and mirror cartridge 66 may thus be added or loaded into the handle 12 and mirror housing 20, respectively, from opposite ends and in opposite directions.

Assembly may further include inserting a connector 50 (not shown in FIG. 12) into the handle 12. The connector 50 may be for connecting the handle 12 to a remote controller 52 for causing the drive shaft 32 to rotate. In accord with the example of FIG. 5, assembly may further include connecting a motor 56 to a drive shaft proximal end 58 and attaching the motor 56 to the connector 50 for receiving power from the remote controller 52.

In accord with the example of FIG. 4, assembly may further include attaching the connector 50 to a drive shaft proximal end 58 where the connector 50 may be for connection to a drive cable 54 that is caused to be rotated by the remote controller 52.

In accord with the example of FIG. 6, assembly may further include connecting a knob 60 to a drive shaft proximal end 58 for manually rotating the drive shaft 32.

In accord with some examples, the mirror cartridge 66 may further include at least one elongated bearing member 68 connected to the base 24 and in contact with a film top surface 46.

In accord with the example of FIG. 9, assembly may include attaching a hydrophilic material to at least a portion of the at least one elongated bearing member 68 for absorbing moisture from the film top surface 46. In addition, assembly may include where the hydrophilic material forms a cylinder 70 and rotatably mounting the cylinder 70 on the at least one elongated bearing member 68 such that the cylinder 70 rotates as the film 30 moves.

As described above, a method of assembling a dental mirror may comprise the steps of:

providing a mirror cartridge including a base, a film-roller bearing connected to the base, and a film support structure connected to the base;

inserting a film over the film support structure;

rotatably mounting a film-roller onto the film-roller bearing;

inserting the mirror cartridge into a cartridge opening of a mirror housing; and inserting a drive shaft into a lumen of a handle connected to the mirror housing such that a distal end of the drive shaft and a proximal end of the film-roller are rotatably linked such that a rotation of the drive shaft rotates the film-roller causing the film to move relative to the film support structure.

The method may further include inserting a connector into the handle wherein the connector is for connecting the handle to a remote controller for causing the drive shaft to rotate.

The method may further include connecting a motor to a drive shaft proximal end and attaching the motor to the connector wherein the connector is for receiving power from the remote controller.

The method may further include attaching the connector to a drive shaft proximal end wherein the connector is for connection to a drive cable that is caused to be rotated by the remote controller.

The method may further include connecting a knob to a drive shaft proximal end for manually rotating the drive shaft.

The mirror cartridge may also include at least one elongated bearing member connected to the base and in contact with a film top surface.

The method may further include attaching a hydrophilic material to at least a portion of the at least one elongated bearing member for absorbing moisture from the film top surface.

The hydrophilic material may also form a cylinder and include rotatably mounting the cylinder on the at least one elongated bearing member such that the cylinder rotates as the film moves.

A further example embodiment is shown and described with respect to FIGS. 13 and 14. The dental mirror of FIG. 13 is similar to the dental mirror examples above with the addition of an illumination source 82 (shown in FIG. 14) contained within the handle 84 for illuminating an area, shown at 86 in FIG. 14, in front of the mirror housing 20. The illumination source 82 may be any suitable light source, such as an LED or any conventional light bulb. Illumination source 82 may also provide any desired color or spectrum of light desired or may include multiple colored light sources or filters to allow a user to change the color of light emitted to enhance the user's ability to visualize target areas.

A wireless receiver 88 (shown in FIG. 14), for communication with a wireless transmitter 89, may be contained within the handle 84 and connected to at least one of the motor 90 that is connected to the drive shaft proximal end 92 and the illumination source 82. The connection of wireless receiver 88 to illumination source 82 is not shown for clarity. Transmitter 89 may include control buttons 94, 96 for controlling the motor 92 and/or illumination source 82. The transmitter 89 allows an assistant to enable the motor 92 to rotate the drive shaft and scroll the film to provide a fresh, clean reflective surface or to adjust illumination source in response to a voice command by a dentist. This allows the dentist to remain focused on the procedure without distraction. The illumination source may further include an adjustable luminosity control that may be brightened or dimmed using control button 96. Alternately or additionally, handle 84 may include a button 98 that a user may periodically activate the motor to advance the film without the need for an assistant.

The dental mirror example may further include an embodiment where each of the motor 90 and the illumination source 82 are powered by a battery 100 contained within the handle 84, as shown in FIG. 14. Further and in order to provide an economical and durable dental mirror, an embodiment where the motor, the illumination source, the wireless receiver, and the battery form a portion of an electronics cartridge 102 may be removable from the handle 84. Providing a removable electronics cartridge allows the remainder of the dental mirror to be sterilized, such as by autoclaving, while avoiding exposing the electronics to the harsh and corrosive sterilization procedure.

Light from illumination source 82 may be transmitted to window or lens 104 by any acceptable light guide or combination of light transmissive structures. The example shown at FIG. 14 shows illumination source 82 coupled to a light tube or fiber optic 106 that carries light to a sleeve bearing 108 that may be formed of transparent material to allow light to pass from light tube 106 to lens 104. Sleeve bearing 108 in other respects is similar to sleeve bearing 33 described above. As those skilled in the art will appreciate, any of the light tube and the sleeve bearing 108 may be treated with coatings, sleeves, or other treatments to ensure an acceptable amount of light is transmitted from illumination source 82 to lens 104. Alternatively, bearing sleeve 108 may have a channel or a slit to accommodate a length of fiber optic 106 from illumination source 82 to lens 104.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

What is claimed is:

1. A dental mirror comprising:
a handle having a lumen extending from a handle distal end to a handle proximal end;
a mirror housing attached to the handle proximal end;
a mirror cartridge for insertion through a cartridge opening of the mirror housing, the mirror cartridge including a base, a film-roller bearing connected to the base, a film support structure connected to the base, a film surrounding the film support structure, and at least one elongated bearing member connected to the base and in contact with a film top surface;
a drive shaft rotatably held within the handle;
a film-roller rotatably attached to the film-roller bearing; and
wherein a distal end of the drive shaft and a proximal end of the film-roller are rotatably linked such that a rotation of the drive shaft rotates the film-roller causing the film to move relative to the film support structure.

2. The dental mirror of claim 1 wherein the handle further includes a connector for connecting the handle to a remote controller for causing the drive shaft to rotate.

3. The dental mirror of claim 2 wherein the handle further includes a motor connected to a drive shaft proximal end and the connector is attached to the motor for receiving power from the remote controller.

4. The dental mirror of claim 2 wherein the connector is attached to a drive shaft proximal end and is for connection to a drive cable that is caused to be rotated by the remote controller.

5. The dental mirror of claim 1 wherein the handle further includes a knob connected to a drive shaft proximal end for manually rotating the drive shaft.

6. The dental mirror of claim 1 wherein the mirror housing further includes a peripheral frame defining a film opening for exposing a portion of the film, wherein a top surface of the peripheral frame is formed above a film top surface.

7. The dental mirror of claim 6 wherein structure of the mirror housing defining the cartridge opening includes a portion of the peripheral frame.

8. The dental mirror of claim 1 wherein the base, the film-roller bearing, and the film support structure are molded as a unitary piece, and wherein the handle and the mirror housing are molded as a unitary piece.

9. The dental mirror of claim 1 wherein a hydrophilic material is attached to at least a portion of the at least one elongated bearing member for absorbing moisture from the film top surface.

10. The dental mirror of claim 9 wherein the hydrophilic material forms a cylinder and is rotatably mounted on the at least one elongated bearing member such that the cylinder rotates as the film moves.

11. The dental mirror of claim 1 wherein the mirror cartridge is removably attached to the mirror housing without a use of tools.

12. The dental mirror of claim 1 wherein the drive shaft further includes a sleeve bearing surrounding at least a portion of the drive shaft.

13. The dental mirror of claim 1 wherein the drive shaft and the film-roller are rotatably linked by gears.

14. The dental mirror of claim 1 wherein the film is formed from a flexible reflective material.

15. The dental mirror of claim 1 wherein a mirror surface is formed on a portion of the film support structure.

16. The dental mirror of claim 1 wherein at least a portion of the mirror cartridge is formed of a material that will not withstand autoclave sterilization.

17. The dental mirror of claim 1 wherein at least one of the handle and the mirror housing is formed of a material that will not withstand autoclave sterilization.

18. The dental mirror of claim 1 further including an illumination source contained within the handle for illuminating an area in front of the mirror housing.

19. The dental mirror of claim 18 further including a wireless receiver contained within the handle for communication with a wireless transmitter and wherein the wireless receiver is connected to at least one of the illumination source and a motor connected to a drive shaft proximal end.

20. The dental mirror of claim 19 wherein each of the motor and the illumination source are powered by a battery contained within the handle.

21. The dental mirror of claim 20 wherein the motor, the illumination source, the wireless receiver, and the battery form a portion of an electronics cartridge that is removable from the handle.

22. A mirror cartridge comprising:
a base;
a film-roller bearing connected to the base;
a film support structure connected to the base;
a film surrounding the film support structure;
at least one elongated bearing member connected to the base and in contact with a film top surface: and
wherein the cartridge is for insertion into a dental mirror.

23. The mirror cartridge of claim 22 wherein the base, the film-roller bearing, and the film support structure are molded as a unitary piece.

24. The mirror cartridge of claim 22 wherein a hydrophilic material is attached to at least a portion of the at least one elongated bearing member for absorbing moisture from the film top surface.

25. The mirror cartridge of claim 24 wherein the hydrophilic material forms a cylinder and is rotatably mounted on the at least one elongated bearing member such that the cylinder rotates as the film moves.

26. The mirror cartridge of claim 22 further including a film-roller rotatably connected to the film-roller bearing.

27. The mirror cartridge of claim 22 wherein the mirror cartridge is removably attached to a mirror housing without a use of tools.

28. The dental mirror of claim 22 wherein at least a portion of the mirror cartridge is formed of a material that will not withstand autoclave sterilization.

29. A dental mirror comprising:
a handle having a lumen extending from a handle distal end to a handle proximal end;
a mirror housing attached to the handle proximal end;
a mirror cartridge held within a cartridge opening of the mirror housing, the mirror cartridge including a base, a film-roller rotatably attached to the base, a film support structure connected to the base, a film surrounding the film support structure, and at least one elongated bearing member connected to the base and in contact with a film top surface;
a drive shaft rotatably held within the handle;
wherein a distal end of the drive shaft and a proximal end of the film-roller are rotatably linked such that a rotation of the drive shaft rotates the film-roller causing the film to move relative to the film support structure;
an illumination source contained within the handle for illuminating an area in front of the mirror housing; and
a motor contained within the handle and connected to a proximal end of the drive shaft.

30. The dental mirror of claim 29 wherein the handle further includes a connector for connecting the handle to a remote controller for causing the drive shaft to rotate.

31. The dental mirror of claim 30 wherein the connector is coupled to the motor and the illumination source for receiving power from the remote controller.

32. The dental mirror of claim 29 further including a wireless receiver contained within the handle and connected to at least one of the motor and the illumination source for communication with a wireless transmitter.

33. The dental mirror of claim 32 wherein the motor, the illumination source, the wireless receiver, and the battery form a portion of an electronics cartridge that is removable from the handle.

34. The dental mirror of claim 29 wherein each of the motor and the illumination source are powered by a battery contained within the handle.

* * * * *